( 12 ) United States Patent
Elfsberg et al.

(10) Patent No.: US 8,721,611 B2
(45) Date of Patent: May 13, 2014

(54) ABSORBENT ARTICLE

(75) Inventors: Camilla Elfsberg, Torslanda (SE);
Pontus Winqvist, Stora Höga (SE);
Kent Hermansson, Västra Frölunda (SE)

(73) Assignee: SCA Hygiene Products AB, Göteborg (SE)

( * ) Notice: Subject to any disclaimer, the term of this patent is extended or adjusted under 35 U.S.C. 154(b) by 747 days.

(21) Appl. No.: 12/513,565

(22) PCT Filed: Nov. 7, 2006

(86) PCT No.: PCT/EP2006/010647
§ 371 (c)(1),
(2), (4) Date: May 5, 2009

(87) PCT Pub. No.: WO2008/055520
PCT Pub. Date: May 15, 2008

(65) Prior Publication Data
US 2010/0069873 A1 Mar. 18, 2010

(51) Int. Cl.
*A61F 13/64* (2006.01)
*A61F 13/62* (2006.01)

(52) U.S. Cl.
USPC .................. 604/392; 604/385.01; 604/391

(58) Field of Classification Search
USPC .............. 604/385.23, 385.25, 389–392
See application file for complete search history.

(56) References Cited

U.S. PATENT DOCUMENTS

| D290,780 | S | | 7/1987 | Wistrand |
| 4,883,480 | A | | 11/1989 | Huffman et al. |
| 5,593,401 | A | * | 1/1997 | Sosalla et al. ............ 604/385.28 |
| 5,810,797 | A | * | 9/1998 | Menard et al. ............... 604/378 |
| 5,876,391 | A | * | 3/1999 | Roe et al. .................. 604/385.3 |
| 5,879,341 | A | * | 3/1999 | Odorzynski et al. .......... 604/367 |

(Continued)

FOREIGN PATENT DOCUMENTS

EP 0 172 036 A2 2/1986
EP 0 699 066 B1 10/1997

(Continued)

OTHER PUBLICATIONS

International Search Report (PCT/ISA/210) for PCT/EP2006/010647, completed Jul. 3, 2007.

(Continued)

*Primary Examiner* — Susan Su
(74) *Attorney, Agent, or Firm* — Buchanan Ingersoll & Rooney PC

(57) ABSTRACT

Absorbent article, in particular a diaper or an incontinence product, includes an absorbent structure (1) including a backsheet (20), a top-sheet (22) and an absorbent core (24) there between. The absorbent structure (1) has a front portion (10) defining a front lateral edge (16), a rear portion (14) defining a rear lateral edge (18) and a crotch portion (12) situated between the front portion and the rear portion. A pair of belt sections (30, 32) is present for fastening the absorbent article to the waist of a wearer, the belt sections being fixedly attached to the rear portion of the absorbent structure. The absorbent article has a maximum lateral extension B between the respective lateral-most edges (302, 322) of the belt sections that is governed by the following expression: $0.3<A/B<0.7$ where A is the maximum lateral extension of the front lateral edge of the absorbent structure.

34 Claims, 9 Drawing Sheets

(56) References Cited

U.S. PATENT DOCUMENTS

| | | | |
|---|---|---|---|
| 5,993,433 A * | 11/1999 | St. Louis et al. | 604/385.27 |
| 6,110,157 A | 8/2000 | Schmidt | |
| 6,132,410 A * | 10/2000 | Van Gompel et al. | 604/385.25 |
| 6,217,563 B1 * | 4/2001 | Van Gompel et al. | 604/385.101 |
| 6,231,557 B1 * | 5/2001 | Krautkramer et al. | 604/385.16 |
| 6,316,687 B1 * | 11/2001 | Davis et al. | 604/372 |
| 6,334,858 B1 * | 1/2002 | Ronnberg et al. | 604/392 |
| 6,342,050 B1 * | 1/2002 | Ronnberg et al. | 604/392 |
| 6,494,873 B2 * | 12/2002 | Karlsson et al. | 604/392 |
| 6,572,596 B2 * | 6/2003 | Pargass et al. | 604/385.01 |
| 6,607,515 B2 * | 8/2003 | Glaug et al. | 604/385.01 |
| 6,659,990 B1 * | 12/2003 | Odorzynski et al. | 604/385.01 |
| 6,669,678 B2 * | 12/2003 | Hermansson et al. | 604/392 |
| 6,676,648 B2 * | 1/2004 | Bruemmer Prestley et al. | 604/385.23 |
| 6,726,670 B2 * | 4/2004 | Almberg et al. | 604/392 |
| 6,764,479 B2 * | 7/2004 | Kusibojoska et al. | 604/385.3 |
| 7,435,244 B2 * | 10/2008 | Schroer et al. | 604/385.27 |
| 7,708,728 B2 * | 5/2010 | Arizti et al. | 604/385.27 |
| 7,785,307 B2 * | 8/2010 | Wennerback | 604/385.01 |
| 7,789,868 B2 * | 9/2010 | Tachibana | 604/385.23 |
| 7,815,620 B2 * | 10/2010 | Coates et al. | 604/392 |
| 7,828,785 B2 * | 11/2010 | Back | 604/392 |
| 8,083,880 B2 * | 12/2011 | Kurata | 156/227 |
| 2001/0034511 A1 * | 10/2001 | Hermansson et al. | 604/386 |
| 2002/0038110 A1 * | 3/2002 | Kusibojoska et al. | 604/392 |
| 2002/0042600 A1 * | 4/2002 | Datta et al. | 604/385.13 |
| 2002/0095132 A1 * | 7/2002 | Ashton et al. | 604/392 |
| 2002/0123732 A1 * | 9/2002 | Koyama et al. | 604/385.24 |
| 2002/0138065 A1 * | 9/2002 | Yeater et al. | 604/395 |
| 2002/0151863 A1 * | 10/2002 | Toyoshima | 604/385.29 |
| 2003/0060795 A1 * | 3/2003 | Almberg | 604/392 |
| 2003/0083634 A1 * | 5/2003 | Fernfors | 604/385.3 |
| 2003/0135192 A1 * | 7/2003 | Guralski et al. | 604/391 |
| 2004/0122413 A1 * | 6/2004 | Roessler et al. | 604/386 |
| 2004/0153046 A1 | 8/2004 | Ito et al. | |
| 2005/0137544 A1 * | 6/2005 | Schroeder et al. | 604/367 |
| 2005/0171500 A1 * | 8/2005 | Koyama et al. | 604/385.28 |
| 2006/0004339 A1 * | 1/2006 | Lord et al. | 604/385.3 |
| 2006/0041240 A1 * | 2/2006 | Erdman | 604/385.28 |
| 2007/0066954 A1 * | 3/2007 | LaVon et al. | 604/392 |
| 2007/0093772 A1 * | 4/2007 | Koyama et al. | 604/385.27 |
| 2007/0287982 A1 * | 12/2007 | Lodge et al. | 604/402 |
| 2008/0033389 A1 * | 2/2008 | Bandorf et al. | 604/392 |
| 2008/0071240 A1 * | 3/2008 | Erdman et al. | 604/365 |
| 2008/0154227 A1 * | 6/2008 | Andersson et al. | 604/385.22 |
| 2008/0188822 A1 * | 8/2008 | Lodge et al. | 604/385.03 |
| 2008/0294137 A1 * | 11/2008 | Jansson | 604/385.23 |
| 2009/0018520 A1 * | 1/2009 | Tachibana | 604/385.23 |
| 2009/0157028 A1 * | 6/2009 | Back | 604/365 |
| 2010/0004616 A1 * | 1/2010 | Nakamura et al. | 604/389 |
| 2010/0268186 A1 * | 10/2010 | Lornell et al. | 604/392 |
| 2011/0046597 A1 * | 2/2011 | Mizutani et al. | 604/385.25 |

FOREIGN PATENT DOCUMENTS

| | | |
|---|---|---|
| EP | 1 137 384 B1 | 2/2004 |
| JP | S58-059823 U | 6/1984 |
| JP | S60-119944 A | 6/1985 |
| JP | S60-181302 A | 9/1985 |
| JP | S61-124602 A | 6/1986 |
| JP | H08-510145 A | 10/1996 |
| JP | H09-502637 A | 3/1997 |
| JP | H10-155833 A | 6/1998 |
| JP | 2002-253608 A | 9/2002 |
| JP | 2002-529149 A | 9/2002 |
| JP | 2004-503329 A | 2/2004 |
| JP | 2005-500135 A | 1/2005 |
| JP | 2005-500136 A | 1/2005 |
| WO | WO 84/04242 A1 | 11/1984 |
| WO | WO 94/26222 A1 | 11/1994 |
| WO | WO 95/07677 A1 | 3/1995 |
| WO | WO 00/27330 A1 | 5/2000 |
| WO | WO 02/05739 A1 | 1/2002 |
| WO | 03/017904 A1 | 3/2003 |
| WO | WO 03/017902 A1 | 3/2003 |

OTHER PUBLICATIONS

Written Opinion (PCT/ISA/237) for PCT/EP2006/010647, completed Jul. 3, 2007.

Notice of Reasons for Rejection dated Dec. 6, 2011 issued in the corresponding Japanese Patent Application No. 2009-534990.

* cited by examiner

ABSORBENT ARTICLE

TECHNICAL FIELD

The present invention refers to an absorbent article, in particular, a diaper or an incontinence product and, more specifically, to an adult incontinence product. Absorbent articles of this kind usually comprise an absorbent structure including a back-sheet, a top-sheet and an absorbent core there between, whereas the top-sheet is intended to be directed towards the user when the absorbent article is worn. To fasten the absorbent article around the waist of a wearer, a fastening system is provided on the absorbent structure, typically in the form of a belt system.

BACKGROUND OF THE INVENTION

Absorbent articles, in particular adult incontinence products, are worn by the respective wearer typically over a considerable period and on a day-to-day basis. Accordingly, a comfortable fit of the absorbent article is crucial in order to increase the well-being of the wearer. In the case of adult incontinence products, absorbent articles that are worn around the lower part of the trunk are usually used by bed-ridden people, in particular elderly people. Depending on their mental state and activity level, different types of incontinence products are usually used to accommodate for the wearer's specific needs. Incontinence products that are applied to bedridden people are usually applied to the wearer by nursing staff in the respective homes.

Accordingly, a balance has to be found between a tight fit of the incontinence product in order to reduce the occurrence of leaks and/or shifting of the absorbent article due to movements of the wearer, the actual wearing comfort in order to increase the well-being of the wearer of the product, and a good applicability to facilitate convenient, quick and trouble-free application of the incontinence product, in particular by nursing staff.

SUMMARY OF THE DISCLOSURE

It is an object of the present invention to provide an absorbent article, in particular a diaper or an incontinence product, which provides a comfortable fit of the absorbent article to a wearer and has improved handling and/or application characteristics.

These objects are achieved by an absorbent article, in particular a diaper or an incontinence product, with the features of claim 1.

The absorbent article according to claim 1 comprises an absorbent structure including a back-sheet, a top-sheet and an absorbent core there between. The absorbent structure has a front portion defining a front lateral edge, a rear portion defining a rear lateral edge, and a crotch portion situated between the front portion and the rear portion. Furthermore, a pair of belt sections for fastening the absorbent article to the waist of a wearer is provided, the belt sections being fixedly attached to the rear portion of the absorbent structure, wherein the absorbent article has a maximum lateral extension B between the respective lateral-most edges of the belt sections that is governed by the following expression:

$$0.3 < A/B < 0.7$$

where A is the maximum lateral extension of the front lateral edge of the absorbent structure.

Preferably, the dimensions of the absorbent article are governed by the expression $0.35 < A/B < 0.65$, more preferred $0.4 < A/B < 0.6$, even more preferred $0.45 < A/B < 0.55$, and most preferred $A/B = 0.5$.

The term "maximum lateral extension" is to be understood in a sense that the respective section of the absorbent article is completely stretched out, in particular when the section also includes an elastic section. The maximum lateral extension B of the lateral-most edges of the belt sections is measured when the belt sections are stretched out laterally and any elastic portion is fully extended in the lateral direction. The maximum lateral extension is then measured between the two lateral-most, or most remote, edges of the belt sections.

The term "absorbent structure" is intended to mean that this structure includes an absorbent section, in particular an absorbent core. It will be understood, however, that not necessarily the entire absorbent structure is made to actually absorb liquids. In particular, extending areas of the absorbent structure, in which the absorbent core is not present, are typically not intended to absorb liquids but to serve rather as a structure that is used to keep the absorbent core in its preferred, or intended, position when fitted to a wearer.

An absorbent article with the above-given specific ratio of the maximum lateral extension B between the distal-most edges of the belt sections and the maximum lateral extension A of the front lateral edge of the back-sheet solve the above-mentioned object. In particular, the given ratio ensures that the belt sections do not overlap with one another when the absorbent article is fastened around the waist of a wearer. In particular, the belt sections do not overlap with one another on the front portion of the absorbent structure. This has the advantage that the absorbent article has reduced bulk where the belt sections are fastened to the front portion of the absorbent structure such that a comfortable and slim fit of the worn absorbent article and appearance can be achieved. Furthermore, due to the reduced number of layers in the fattening area of the absorbent article and the thus reduced thickness, the breathability of the absorbent article can be improved such that the skin situated under the portion of the absorbent structure, onto which the pair of belt sections is fastened, can breathe more easily. Additionally, a better heat exchange is secured due to the reduced number of layers.

Furthermore, the handling of the absorbent article is improved in that the belt sections can be fastened to the front portion of the absorbent structure easily and can be easily and symmetrically adjusted, since the belt sections do not overlap. In contrast, a perfectly symmetrical adjustment of the belt sections is difficult to achieve when the belt sections overlap on a landing zone of the absorbent structure since the belt sections then necessarily have to be fastened one after another (i.e. sequentially). According to the absorbent article of the present disclosure, however, the two belt sections can be fastened simultaneously such that the user can adjust the fit of the absorbent article to the wearer more evenly.

Additionally, the given geometry has the advantage that the user applying the absorbent article to a wearer, in particular nursing staff or a guardian, can grasp both belt sections easily with one hand, such that the other hand may hold the absorbent structure in place or manage the wearer. This is possible since the lateral-most edges of the belt sections are spaced apart from one another only by a small distance when the belt sections are fastened to a landing zone on the front portion of the absorbent structure. Accordingly, in the instant before the lateral-most edges of the free belt ends are actually attached to this landing zone, they are also spaced apart from one another, basically by the same amount, typically about 3 to 6 cm. In this configuration, the user can easily grasp both free belt ends with one hand, without any overlapping of the belt ends, and adjust the front portion of the absorbent structure with the other hand before simultaneously attaching both free belt ends to the landing zone with one hand.

It will be appreciated that the user, in particular the nursing staff or the guardian, can also open the belt sections simultaneously with one hand after use of the article. This is in particular the case when the belt sections are spaced from one another in the fitted position only by 3 to 6 cm.

In addition to that, the dimensions of the belt sections also allow packaging of the belt sections in a favourable manner, namely such that the lateral-most edges of the belt sections are situated close to one another in the packaged state of the absorbent article such that the user can grasp the two belt sections simultaneously with one hand. The other hand can then be used, again, to either manage the wearer or to adjust the absorbent structure to the wearer.

In a preferred embodiment, the front portion of the absorbent structure includes a first elastic section such that the front portion is generally elastically extendable in the lateral direction. In another preferred embodiment, the rear portion includes a second elastic section such that the rear portion is generally elastically extendable in the lateral direction. In a preferred embodiment, the absorbent structure includes leg elastics in the crotch portion, such that the crotch portion is generally elastically extendable in the longitudinal direction of the absorbent structure. In yet another preferred embodiment, the absorbent structure includes elastic front side panels and/or elastic rear side panels such that the side panels are generally extendable at least in the lateral direction of the absorbent structure.

The provision of the different elastic areas within the absorbent structure can improve the wearing comfort of the absorbent article significantly and may reduce the occurrence of leaks. This is in particular due to the fact that the absorbent structure is held relatively closely to the body of the wearer by the elastic sections but allows for movements of the wearer as well as for sitting and standing postures, and accommodates for the breathing movements of the abdomen. The different arrangements can also reduce the effect the belt sections have on the skin, in particular red stripes on the skin.

The belt sections according to this design can be made from a generally non-elastic material. A significant advantage of using non-elastic material for the belt sections is that the non-elastic belts are easier to handle in a production machine than elastic belt sections. Furthermore, belt connectors are easier to apply to non-elastic belt sections. However, in combination with the elastically extendable first and/or second elastic sections and/or the elastic front side panels and/or rear side panels, this arrangement still leads to a superior fit of the absorbent article, even when the wearer wears the absorbent article in different postures, for example sitting and standing.

In a preferred embodiment, the back-sheet has a centre-line extending in the longitudinal direction of the back-sheet and the belt sections are arranged symmetrically with respect to this centre-line. In particular, the absorbent article can be generally symmetrical with respect to the centre-line. It is particularly preferred that both belt sections have the same length. Due to the symmetrical design of the absorbent article with respect to a longitudinally extending centre-line, the load and pressure distribution on the wearer is also symmetrical. In other words, a symmetrical design of the absorbent article reduces an uneven balance of the absorbent article, in particular when it has already absorbed some amount of liquid. Furthermore, the handling is improved since the person applying the absorbent article to a wearer can carry out two identical movements for fastening the belt sections. In addition to that, it is easier and more intuitively to understand for the user how the symmetrical absorbent article is to be used, which also improves the handling of the article.

In addition to the advantages mentioned above, a symmetrical design has the advantage of an easier manufacture compared to asymmetrical designs since the handling of the absorbent article can be the same on both sides of the production line. In addition to that, the design can also improve the efficiency of material usage.

In a preferred embodiment, at least one belt connector is situated on each of the belt sections, the belt connectors being arranged to be connectable to a landing zone that is situated on the front portion of the absorbent structure. In a particularly preferred embodiment, the belt connectors and the landing zone are made from Velcro™ fasteners, so called hook and loop connectors. The belt connectors may be hook connectors and the outer side of the back-sheet, in particular a back-sheet comprising an outer layer of nonwoven material, serves as a landing zone. Such an article with an outer layer of a nonwoven material, in particular the whole outer layer, has the added advantage of a more textile or underwear-like appearance on the outside which improves the comfort for the wearer.

In another embodiment, the outer sides of the belt sections also serve as a landing zone. The above-mentioned specific belt connectors enable an easy application of the absorbent article to the wearer, in particular an easy adjustment of the belt sections, since the Velcro fasteners or hook and loop fasteners can be refastened, should the absorbent article be not placed or fitted correctly. It will be appreciated that the similar advantages can be achieved by using adhesive pads as the belt connectors and a plastic film as the landing zone, whereas the outer layer of the back-sheet can also be made of the plastic film.

In another embodiment, the absorbent structure has a maximum lateral extension $C$ of the rear lateral edge of the absorbent structure, and the maximum front lateral extension $A$ of the front lateral edge of the absorbent structure and the maximum rear lateral extension $C$ generally have the same dimensions. It is particularly advantageous when the absorbent structure has a maximum lateral extension $C$ of the rear lateral edge that is governed by the following expression:

$$0.8 < C/A < 1.2,$$

where $A$ is the maximum lateral extension of the front lateral edge of the absorbent structure. Preferably, the dimensions of the absorbent structure are governed by the expression $0.85 < C/A < 1.15$, more preferred $0.9 < C/A < 1.1$, even more preferred $0.95 < C/A < 1.05$, most preferred $C/A = 1.0$.

The ratio according to the foregoing, in combination with the ratio of $A/B$ as it is defined above, ensures that the front portion and the rear portion of the absorbent structure do not overlap when the absorbent article is fitted to a wearer. In particular, the front side panels and the rear side panels of the absorbent structure do not overlap in the fitted situation. This has the effect that the absorbent structure does not overlap on the hips or any other part on the sides of the body of the wearer. In other words, in a considerable portion of the circumference around the trunk of the wearer, in particular a portion situated on the hips of the wearer, only the belt sections but no material of the absorbent structure are present. This geometry has the advantage that the hips are exposed to air when the absorbent article is worn. Accordingly, the fit of the absorbent article can be improved in terms of wearing comfort, breathability and ventilation.

In a preferred embodiment, the belt sections are made integral with the back-sheet and/or the top-sheet. In another preferred embodiment, the belt sections are fixedly attached to the outside of the back-sheet and/or the outside of the top-sheet. The term "outside" is to be understood in relative terms to the absorption structure and defines the respective outer borders of the absorption structure. In other words, outside of the back-sheet is the side of the back-sheet that is directed away from the wearer, whereas the outside of the top-sheet is the side of the top-sheet that is directed towards the wearer when the absorbent article is worn. In another preferred embodiment, the belt sections are made in one piece with one another. The complexity of the manufacturing process can be reduced when using the above embodiments and the reliability of the absorbent article can be improved by using one-piece belt sections.

In a preferred embodiment, the back-sheet is made from a liquid impermeable but generally vapour permeable material, in particular a laminate of a liquid impermeable but vapour permeable plastic film and a nonwoven material. Such a material has the advantage of, on the one hand, providing a liquid impermeable barrier for liquids contained on the inside of the absorbent structure, but, on the other hand, enables a vapour exchange with the outside and, thus, improves the wearing comfort.

Another preferred embodiment from a handling and manufacturing standpoint is the provision of the back-sheet and the belt sections from the same material. This leads to a situation in which the number of different materials used in the manufacturing process of the absorbent article can be reduced.

However, the back-sheet and the belt sections can be made from different materials. In particular, the belt sections may comprise a non-woven that has a Shinyakasa-value according to Kawabata of 5 or more. The belt sections and the back-sheet material can thus be adapted specifically to the wearer's specific needs. The specific advantages and measuring principles of this particular feature have also been described in EP 1 137 384 B1 of the present applicant.

In a preferred embodiment, the belt sections comprise a laminate of at least three layers of non-woven bonded together with ultrasonic welding or heat welding and have a binding area of less then 10% of the calculated area of the laminate. The first and second layers may have a bulky structure, in particular, in the form of a carded non-woven. This specific material for the belt sections leads to an improved fit and improved comfort for the wearer. The specific advantages of this particular feature and the measuring principles have also been described in WO 03/017904 A1 of the present applicant.

In a further preferred embodiment, the belt sections have a stiffness value between 10 to 130 g when measured according to the ASTM D 4032-82 circular bend procedure. Belt sections showing these values are particularly suited for the absorbent article. The specific advantages as well as the measuring principles of this particular feature have also been described in EP 0 699 066 B1 of the present applicant.

In a further preferred embodiment, the belt sections comprise a laminate of at least two layers of non-woven bonded together by ultrasonic welding or heat welding, whereas the bonding area is less than 10% based on the total area and the laminated bond is such as to have a tear strength of at least 22 N. The specific advantages of this particular feature as well as the measuring principles have also been described in WO 03/017902 A1 of the present applicant.

In a further preferred embodiment, the belt sections are attached to the rear portion of the absorbent structure in belt attachment portions that are designed such that when each of the belt sections is subjected to a tension force of 35 N acting along the longitudinal direction of the belt section and said longitudinal direction of the belt section creates an angle $\alpha$ to the lateral direction of the absorbent structure, the following minimum average release time of each belt section from the absorbent structure are attained:

when $\alpha=10°$, $t\ll 720$ s;
when $\alpha=20°$, $t\ll 330$ s;
when $\alpha=25°$, $t\ll 240$ s;
when $\alpha=30°$, $t\ll 180$ s; and
when $\alpha=40°$, $t\ll 75$ s.

A belt section that is attached to the absorbent structure in this manner functions satisfactorily while it still keeps the manufacturing costs as low as reasonably possible. The specific advantages of these particular features as well as the measuring principles have also been described in WO 02/05739 A1 of the present applicant.

In another preferred embodiment, the belt attachment portions are generally situated on the elastic rear side panels. This leads to a situation in which the belt sections are generally elastically extendable by means of the elastic rear side panels.

It should be noted that, whilst the term "absorbent article" has been used particularly in conjunction with incontinence, and particularly adult incontinence, the invention is not limited to this particular use or any particular size or type of absorbent article implied thereby and it is clear for the skilled person that such belt sections could be used with baby's or children's nappies (diapers) for example, merely by adapting the dimensions appropriately.

BRIEF DESCRIPTION OF THE DRAWINGS

Various exemplary embodiments of the invention will now be described in greater detail by way of example only with reference to the attached drawings, in which.

DETAILED DESCRIPTION OF PREFERRED EMBODIMENTS OF THE DISCLOSURE

Figure 1:
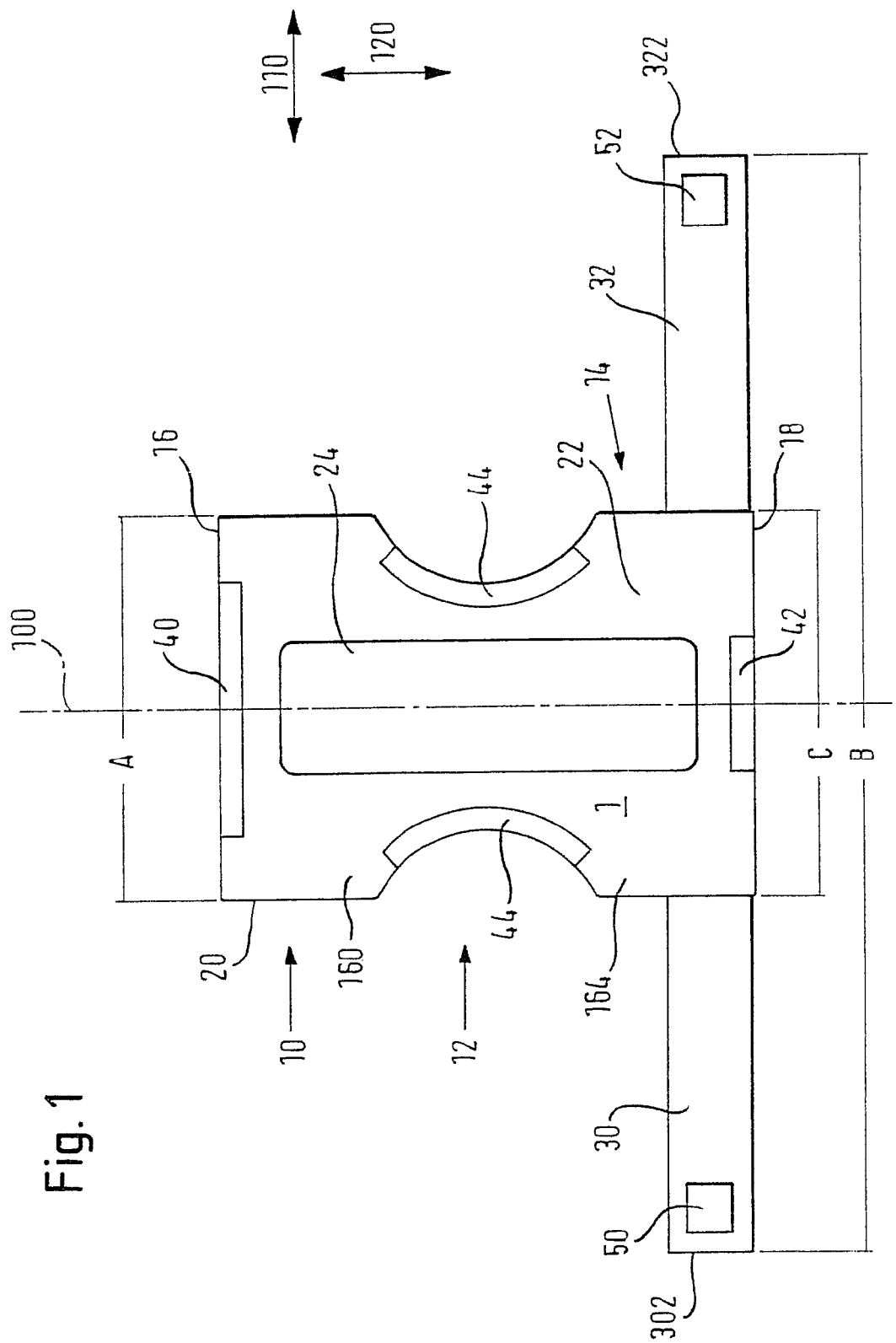
FIG. 1 is a schematic top view of an absorbent article in a first embodiment, showing the side of the article that is directed towards the user when the absorbent article is worn.

Preferred embodiments of the disclosed absorbent article will now be described in detail with reference to the drawings, wherein like reference numerals identify similar or identical elements and repeated description of these features in the respective embodiments is omitted.

Figure 2:
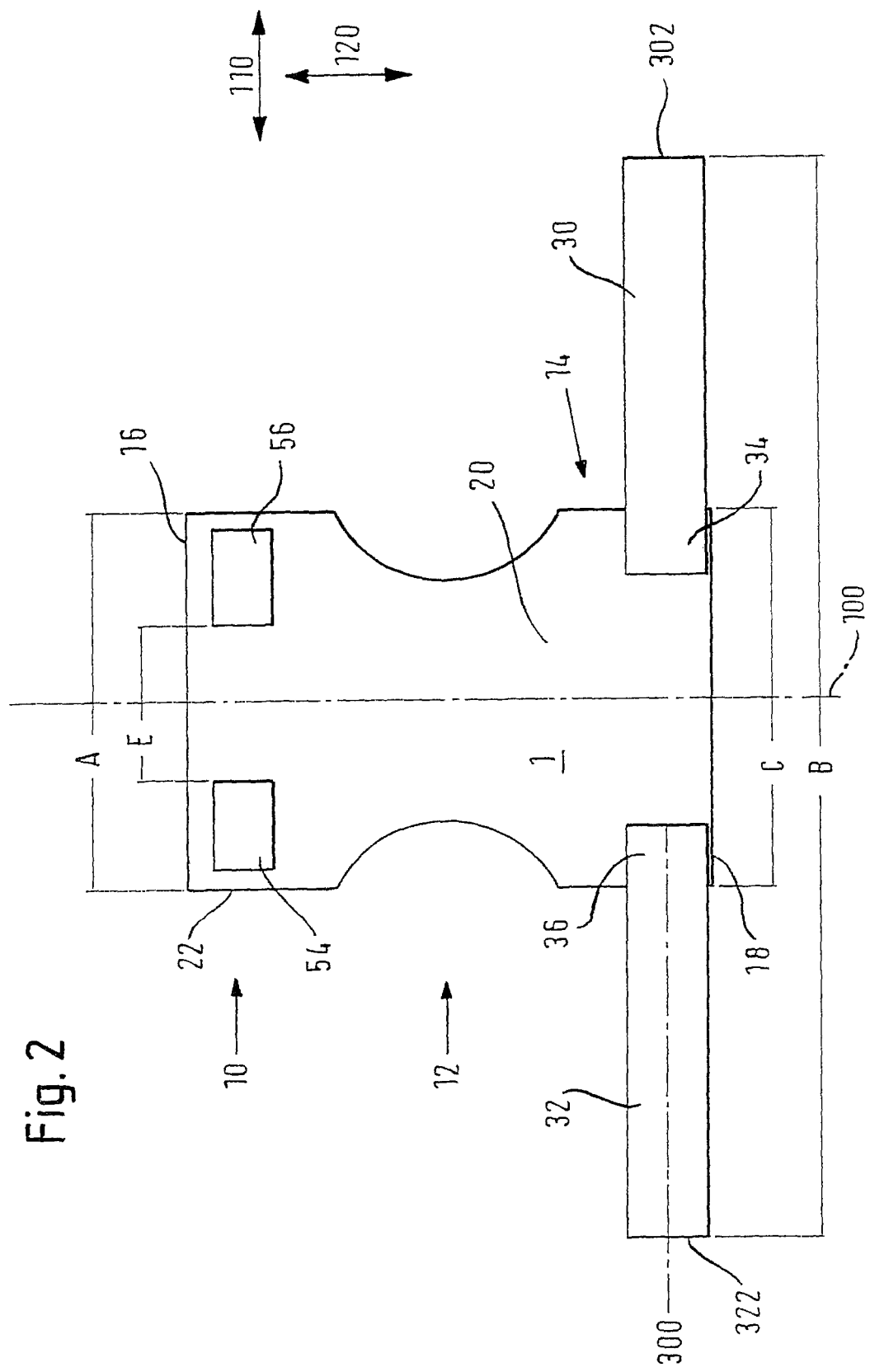
FIG. 2 is a schematic top view on the absorbent article of the first embodiment shown in FIG. 1 from the opposite side, namely the side that is directed away from the user when the article is worn.

FIG. 1 is a schematic top view of an absorbent article in a first embodiment, showing the side of the absorbent article that is directed towards the user when the absorbent article is worn whereas FIG. 2 is a schematic top view on the absorbent article of the first embodiment shown in FIG. 1 from the opposite side, namely the side that is directed away from the user when the article is worn.

The absorbent article comprises an absorbent structure 1 that is generally made up of an absorbent core 24 that is sandwiched between a generally liquid permeable top-sheet 22 and a generally liquid impermeable back-sheet 20. The absorbent structure 1 has a front portion 10 that is generally worn on the front side (abdomen side) of the wearer, a rear portion 14 that is generally worn on the rear side of the wearer (back side), and a crotch portion 12 that is generally worn in the crotch region of the wearer.

However, although the terms "front portion" and "rear portion" imply the intended orientation of the absorbent article on the wearer, they are intended to be seen as relative terms only. Accordingly, some users might find it appropriate using the absorbent article in a different orientation, in particular the other way round with the "front portion" placed on the back of the wearer.

The top-sheet 22 and the back-sheet 20 usually extend beyond the extension of the absorbent core 24 in the plane of the absorbent core 24 along the full circumference of the absorbent core. The top-sheet 22 and the back-sheet 20 can be joined together by heat welding, ultrasonic welding, glue or any other suitable means or method.

The absorbent core 24 and the top-sheet 22 are intended to be directed towards the wearer when the absorbent article is worn by a wearer. In the rare situation that a top-sheet is not present, the absorbent core 24 would be situated on the back-sheet 20 such that it is intended to be directed towards the wearer when the absorbent article is worn.

Front side panels 160 and rear side panels 164 are formed in the absorbent structure 1. The side panels 160, 164 in combination with the narrow crotch portion 12 give the absorbent structure 1 the typical "hourglass" shape of an absorbent article that is to be worn around the lower part of the trunk. The term "side panels" identifies the areas of the absorbent structure 1 that extend to the outside in the lateral direction 110, basically starting from a virtual longitudinal line crossing through the narrowest portion in the crotch portion 12 of the absorbent structure 1.

The back-sheet 20 of the absorbent structure 1 is generally made from a liquid impermeable material. The liquid impermeable material serves as a liquid barrier for any liquid contained within the absorbent structure 1 and basically prevents the liquid from leaking to the outside. This liquid barrier has to be present at least in the area of the absorbent core 24. However, in order to increase the comfort for a wearer, the liquid impermeable back-sheet 20 can be made from a vapour permeable material such that the absorbent structure 1 can "breathe". Such a vapour permeable back-sheet 20 can be made out of a liquid impermeable, but vapour permeable thin plastic film that is laminated together with a nonwoven material. In this laminate, the plastic film functions as the liquid barrier and the nonwoven gives the laminate mechanical strength and provides the absorbent article with a clothing-like appearance. Such a clothing-like, or rather underwear-like, appearance is particularly appreciated when it is used in incontinence products that are worn by adults on a day to day basis.

It is also contemplated to use as a back-sheet 20 a nonwoven material that is laminated to a liquid impermeable plastic film only in the area in which the absorbent core 24 is present but provide no liquid barrier in the other areas in order to further increase the breathability of the absorbent structure and the wearing comfort for the user.

With regard to the geometry of the absorption structure 1, the longitudinal end of the front portion 10 defines a front lateral edge 16.

The terms "lateral" and "longitudinal" are defined with regard to a centre-line 100 of the absorbent structure 1 and the lateral direction is generally indicated by the reference numeral 110 and the longitudinal direction is generally indicated by the reference numeral 120, as can be seen in the Figures.

A pair of belt sections 30, 32 for fastening the absorbent article around the waist of a wearer is fixedly attached to the outside of the back-sheet 20 in the rear portion 14 of the absorbent structure 1 in belt attachment portions 34, 36. Naturally, the belt sections 30, 32 could also be attached to the absorbent structure 1 in belt attachment portions 34, 36 that are situated on the top-sheet 22 or between the back-sheet 20 and the top-sheet 22. The belt sections 30, 32 are made to extend in laterally opposite directions from the absorbent structure 1, basically along the longitudinal direction 300 of the generally longitudinally-extended belt sections 30, 32, as shown in FIGS. 1 and 2.

The measure B, that is the maximum lateral extension between the lateral-most edges 302, 322 of the belt sections 30, 32 relates actually to the maximum outstretched distance between the lateral-most edges 302, 322 of the belt sections 30, 32. This is irrespective of the fact that the belt sections 30, 32 are fixedly attached to the rear portion 14 of the absorbent structure 1 and may have material of the absorbent structure 1 bridging between the two belt sections 30, 32. In other words, the measure B indicates the distance between the lateral-most edges 302 and 322 of the belt sections 30, 32 in the state in which the belt sections are fitted to the absorbent structure 1, including any parts of absorbent structure between the belt sections. In the case that an elastic section 42 (described in detail below) is present, the maximum extension B is the extension between the lateral-most edges 302, 322 when the elastic section 42 is in its expanded state.

As can be seen in FIGS. 1 and 2, the ratio between the maximum lateral extension A of the front lateral edge 16 of the absorbent structure 1 and the maximum lateral extension B between the respective lateral-most edges 302, 322 of the belt sections 30, 32 is 0.3<A/B<0.7, where A is the maximum lateral extension of the front lateral edge 16 of the absorbent structure. However, it will be appreciated that the dimensions of the absorbent article are preferably governed by the expression 0.35<A/B<0.65, preferably 0.4<A/B<0.6, more preferred 0.45<A/B<0.55, most preferred A/B=0.5.

It will be appreciated that this specific ratio between the maximum lateral extension A of the front lateral edge 16 and the maximum lateral extension B between the lateral-most edges 302, 322 of the belt sections 30, 32 results in an absorbent article which leads to a comfortable fit of the absorbent article when the article is worn. This can also be seen in FIGS. 6 to 8 in which the absorbent article is shown in the worn position.

FIGS. 1 and 2 show that the rear portion 14 of the absorbent structure 1 comprises a rear lateral edge 18 that has a maximum lateral extension C. This maximum lateral extension C of the rear lateral edge 18 has generally the same dimensions as the maximum lateral extension A of the front lateral edge 16. In other words, the front and rear lateral edges 16, 18 may basically have the same dimensions in the lateral direction.

However, the absorbent structure 1 has in the embodiment shown, a maximum lateral extension C of the rear lateral edge 18 of the absorbent structure 1 that is governed by the expression $0.8<C/A<1.2$, where A is the maximum lateral extension of the front lateral edge 16. Preferably, the absorbent structure 1 is governed by the expression $0.85<C/A<1.15$, more preferred $0.9<C/A<1.1$, even more preferred $0.95<C/A<1.05$, and most preferred $C/A=1.0$.

Figure 6:
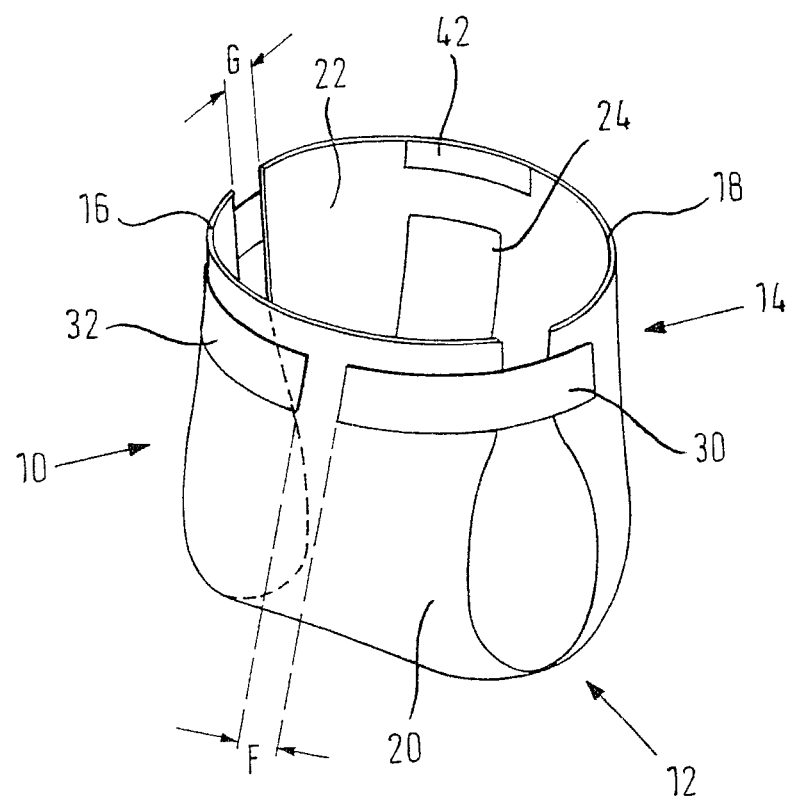
FIG. 6 is a perspective view of the absorbent article shown in FIGS. 1, 2 and 5, with the belt sections fastened to a landing zone.
Figure 7:
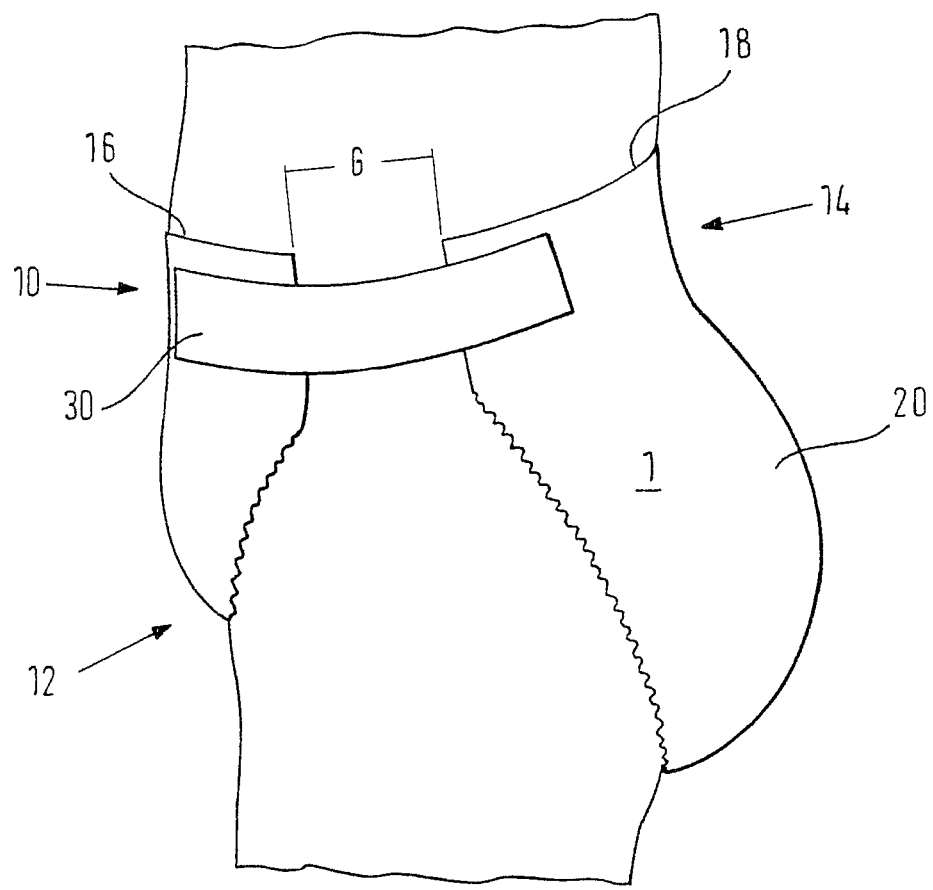
FIG. 7 is a schematic view of the absorbent article of FIGS. 1, 2, 5 and 6 when worn by a wearer.
Figure 8:
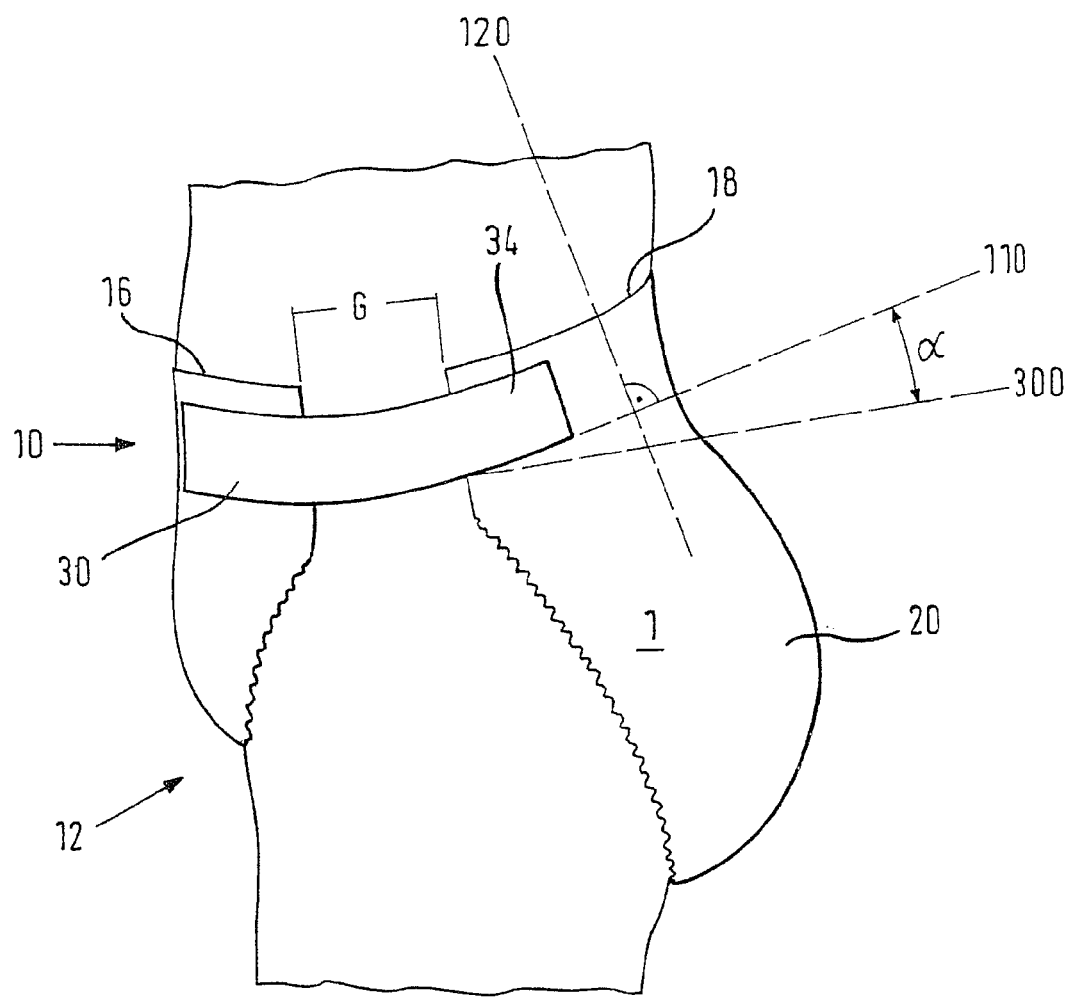
FIG. 8 is the schematic view of FIG. 7, explaining a specific test method.

It becomes immediately clear from FIGS. 6 to 8 that the front portion 10 and the rear portion 14 of the absorbent structure 1, or any side panels 160, 164 of the absorbent structure 1, do not overlap on the hip of the wearer, but there is a considerable gap of a length G that allows air to circulate at the hip. The dimension of the gap G between the front portion 10 and the rear portion 14 of the absorbent structure 1 typically has a dimension of at least 5 cm.

Furthermore, as can be seen particularly well in FIG. 6, the belt sections 30, 32 do not overlap when the absorbent article is worn by a wearer, but their lateral-most edges 302, 322 are spaced apart from one another by a considerable distance F. The gap F between the lateral-most edges 302, 322 of the belt sections 30, 32 when the absorbent article is fitted to a wearer is in a range between 3 and 15 cm, preferably in a range between 3 cm and 6 cm.

The geometry of the absorbent article thus shows the advantage of providing an improved fit, is airy and comfortable to wear, and, reduces the thickness of the absorbent article, leading to a slimmer appearance on the wearer. Furthermore, heat build-up within the article, in particular in the area where the belt sections 30, 32 are fastened to the absorbent structure 1 on the front portion 10, can be reduced. This is mainly due to the reduced number of layers present in the article, compared to a geometry of an absorbent article that has an overlapping belt system.

Figure 4:
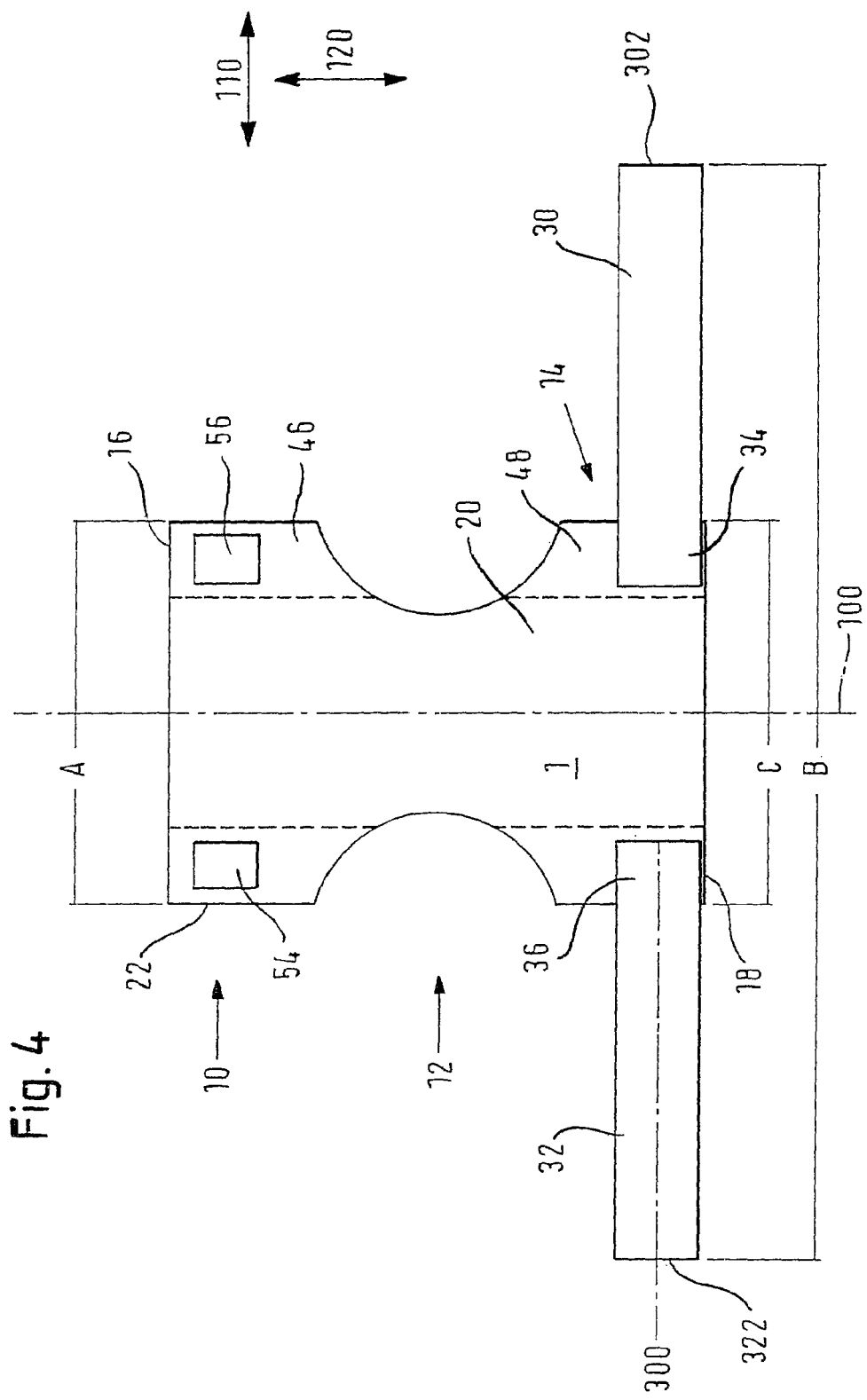
FIG. 4 is a schematic top view on the absorbent article of the second embodiment shown, in FIG. 3 from the opposite side, namely the side that is directed away from the user when the article is worn.
Figure 5:
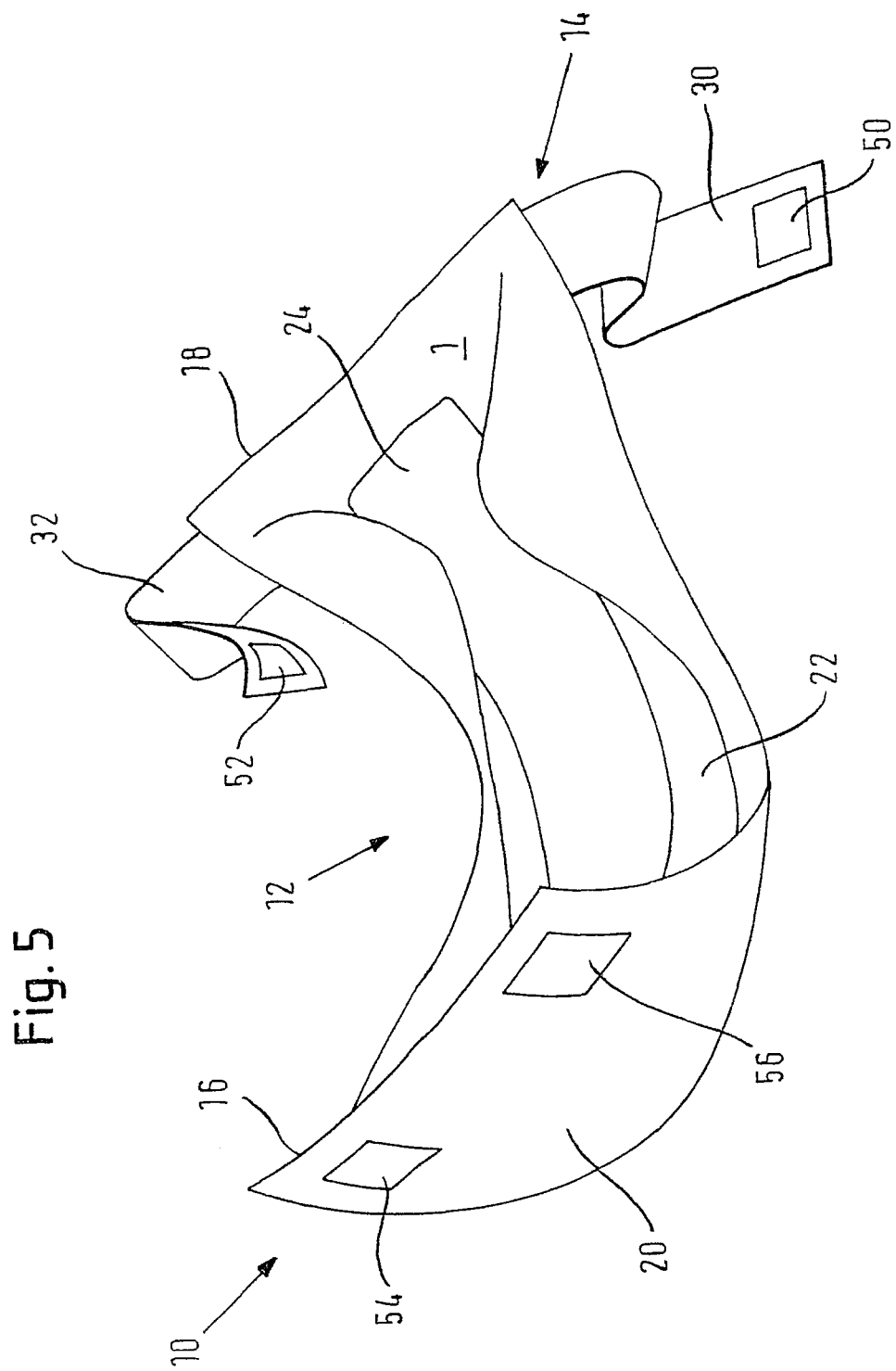
FIG. 5 is a schematic perspective view of the absorbent article shown in FIGS. 1 and 2, in an open position.

As can be derived from FIGS. 1 and 2 in combination with FIGS. 4 and 5, the arrangement of the belt sections in combination with the dimensions of the absorbent structure 1 leads to the unique features of the absorbent article of the present disclosure. In particular, the measures/ratios given above lead to the existence of the gap G between the front portion 10 and the rear portion 14 of the absorbent structure 1 when the absorbent article is fitted around a wearer and, at the same time, result in an arrangement of the belt sections 30, 32, as shown in FIG. 6, such that the belt sections do not overlap in the attached position. On the contrary, a gap F is present between the lateral most edges 302, 322 of the belt sections 30, 32 such that a reduced number of layers can be achieved around the hip of the wearer.

The centre-line 100 extends in the longitudinal direction 120 of the absorption structure 1, and the belt sections 30, 32 are arranged basically symmetrically with respect to the centre-line 100. The belt sections 30, 32 have, in particular, the same length, which leads to an absorbent article that is symmetric with respect to the centre-line 100.

As can be seen particularly well in FIG. 1, at least one belt connector 50, 52 is situated on each of the belt sections 30, 32, the belt connectors 50, 52 being arranged to be connectable to a landing zone or landing zones 54, 56, which are shown in FIG. 2. In particular, the belt connectors 50, 52 can be hook connectors (Velcro™ connectors) and the landing zones 54, 56 can be loop connectors (Velcro™ as well). In a preferred embodiment (not shown), the landing zones 54, 56 are made from the same material as the outer layers of the belt sections 30, 32, whereas the outer layer is to be understood to be the layer that is directed away from the wearer when the absorbent article is worn.

In particular, the belt sections 30, 32 are arranged to be fastened on the back-sheet 20 or on the respective landing zone 54, 56 provided on the back-sheet 20 and are not fastened together when the absorbent article is fitted to the wearer. Accordingly, the belt connectors 50, 52 on the belt sections 30, 32 are situated on the inside of the belt sections, namely on the sides that are intended to be directed towards the wearer when the absorbent article is worn.

In the perspective view of FIG. 5, further features of the absorbent article are shown. In particular, the liquid permeable top-sheet 22 is shown that is attached to the back-sheet 20 on the side of the absorbent structure 1 and is directed towards the user when the absorbent article is worn. The liquid permeable top-sheet 22 preferably has the same outer contour as the back-sheet 20. The liquid permeable top-sheet 22 can be a non-woven with particularly skin friendly properties in order to increase the wearing comfort of the absorbent article even further.

In order to improve the fit of the absorbent article, in Particular when the absorbent article is worn in different positions and/or postures, for example sitting or standing, several elastics are included in the absorbent structure 1. In particular, a first elastic section 40 is present that extends along the front portion 10 of the absorbent structure 1, and a second elastic section 42 is present that extends along its rear portion 14. Furthermore, leg elastics 44 are present that are situated in the crotch portion 12 of the absorbent structure 1 in order to improve the fit of the absorbent article. The leg elastics 44 extend generally in the longitudinal direction 120 of the absorbent article. In a manner known per se in the art, the absorbent article of the present invention may be provided with elasticated leg cuffs to thereby provide improved sealing of the article around the legs of the wearer when worn.

Figure 3:
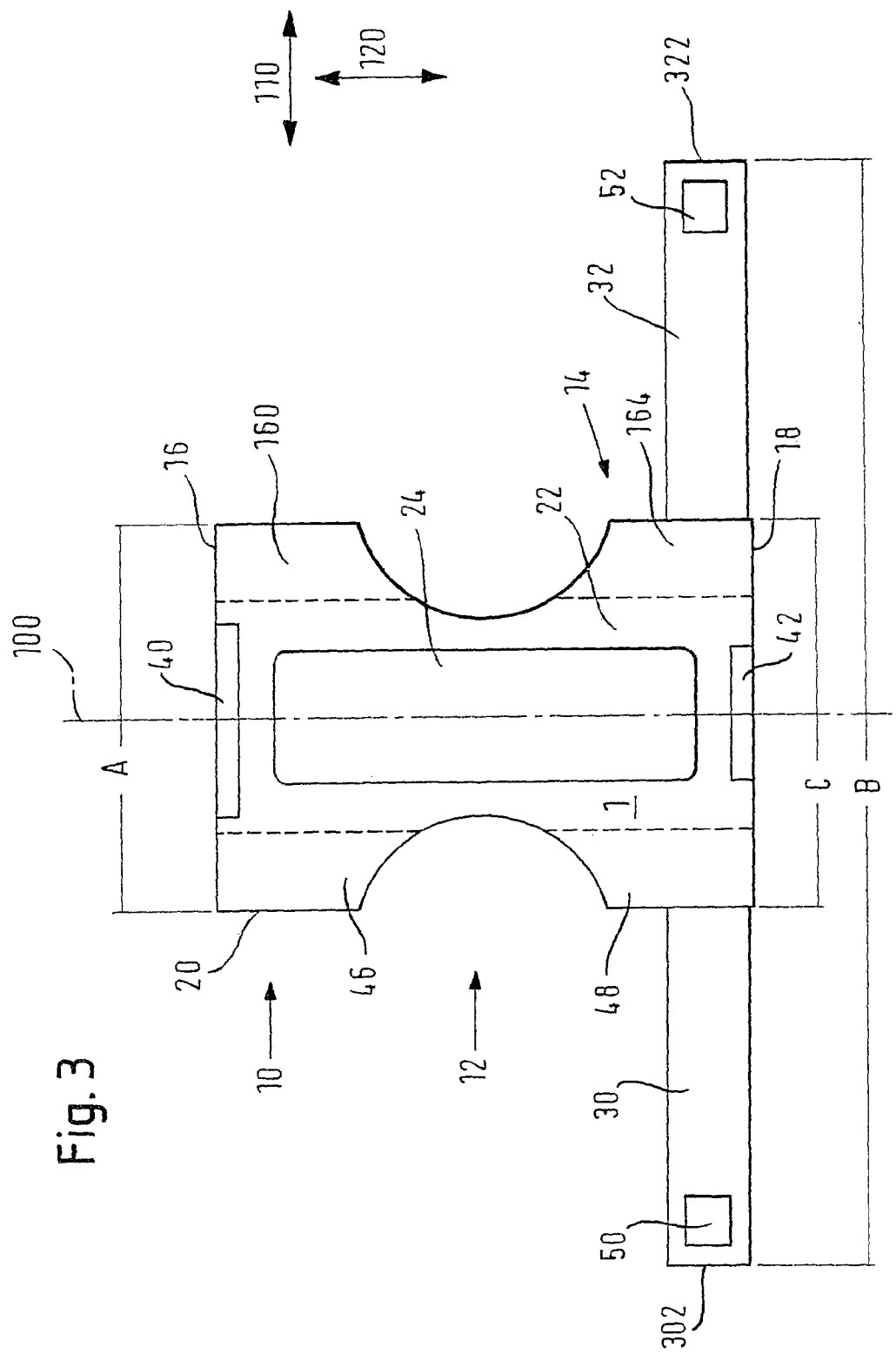
FIG. 3 is a schematic top view of an absorbent article in a second embodiment that includes elastic material in the side panels, showing the side of the article that is directed towards the user when the absorbent article is worn.

In this connection, FIG. 3 and FIG. 4 show an absorbent article in a second embodiment. It will be appreciated that the second embodiment is basically identical to the first embodiment shown in FIGS. 1 and 2, with the exception that the front side panels 160 in the front portion 10 of the absorbent structure 1 include elastic front side panels 46, and the rear side panels 164 in the rear portion 14 of the absorbent structure include elastic rear side panels 48. The elastic front side panels 46 and the elastic rear side panels 48 are generally elastically extendable in the lateral direction 110 of the absorbent article.

It will be understood that in this second embodiment the belt sections 30, 32 are fastened to the outside of the back-sheet 20 of the absorbent structure 1 such that the belt attachment portions 34, 36 are situated on the elastic rear side panels 48. In other words, the belt attachment portions 34, 36 of the belt sections 30, 32 can be elastically moved outwardly in the lateral direction 110 such that the lateral-most edges 302, 322 of the belt sections 30, 32 can be basically extended along with the elastic rear side panels 48. The maximum lateral extension B between the lateral-most edges 302, 322 of the belt sections 30, 32 is, accordingly, measured in the most extended state. Accordingly, it will be appreciated that the maximum lateral extension A of the front lateral edge 16 is also only measured in the most extended state of the elastic front side panel 46.

In addition, the landing zones 54, 56 for the belt connectors 50, 52 are situated on the elastic front side panel 46 such that the landing zones 54, 56 can also be elastically extended outwardly in the lateral direction 110. It will be appreciated that the elastic front side panel 46 and the elastic rear side panel 48 provide thus a structure that improves the fit of the absorbent article to the wearer.

In a preferred embodiment, the belt sections 30, 32 comprise a non-woven that has a Shinyakasa-value according to Kawabata of 5 or more. This value relates to a method used within the textile industry to measure smoothness and flexibility and is disclosed in the literature. The test method in question is used in the textile industry for measuring smoothness and flexibility of a material and is disclosed in "*The Standardization and Analysis of Hand Evaluation* ($2^{nd}$ Edition), Sueo Kawabata, July 1980, *The Hand Evaluation and Standardization Committee, The Textile Machinery Society of Japan*".

Tests have been made with different types of laminates used as belt sections in incontinence articles. It has been found that laminates having a Shinyakasa-value according to Kawabata of 5 or more did not give rise to skin injuries or irritations. Examples of such belt laminates are A: Loosely bonded spunbond of polyethylene, basis weight 40 g/m$^2$, glued in strip-coat pattern to a SOPP (simultaneously oriented polypropylene)—plastic film, 18 μm. Glue amount 3.5 g/m$^2$. The Shinyakasa—value according to Kawabata was 10.37. B: The same as A, but another type of strip-coat pattern at the gluing. The Shinyakasa-value according to Kawabata was 9.74. C: Loosely bonded spunbond of polypropylene, basis weight 40 g/m$^2$, glued in strip-coat pattern to a SOPP (simultaneously oriented polypropylene)-plastic film, 18 μm. Glue amount 3.5 g/m$^2$. The Shinyakasa-value according to Kawabata was 6.88. D: The same as C, but another type of strip-coat pattern at the gluing. The Shinyakasa-value according to Kawabata was 6.22. E: Thermobonded carded nonwoven of polypropylene, basis weight 30 g/m$^2$, glued in full-coat pattern to a SOPP (simultaneously oriented polypropylene)—plastic film, 18 μm. Glue amount 6 g/m$^2$. The Shinyakasa-value according to Kawabata was 8.35. F: The same as E, but another gluing technique. The Shinyakasa-value according to Kawabata was 8.69. G: Thermobonded carded nonwoven of polypropylene, basis weight 35 g/m$^2$, glued in full-coat pattern to a SOPP (simultaneously oriented polypropylene)—plastic film, 18 μm. Glue amount 6 g/m$^2$. The Shinyakasa-value according to Kawabata was 10.22. H: The same as E, but another gluing technique. The Shinyakasa-value according to Kawabata was 10.89.

In another preferred embodiment, the belt sections 30, 32 comprise at least a flexible laminate of at least two layers of non-woven bonded together by ultrasonic welding or heat welding, whereas the bonding pattern has a bonding a tea of no more than 10% and the laminate has a tear strength of at least 22 N. This will make the belt sections resist tearing as the belt sections and the absorbent structure are tightened around the waist of the wearer. Tests have proven that the tearing frequency at normal use for belt sections having a tear strength of 21 N and lower was unacceptably high. Preferably the tear strength should be at least 24 N, more preferably at least 25 N, and most preferably at least 27 N. For those belt sections having a tear strength of 28 N or higher, there was no tearing at all.

A suitable nonwoven material can be a spunbond material, for example, of polypropylene or polyethylene fibres and bi-component fibres may also be used. Another appropriate nonwoven material is a carded thermo-bonded material of e.g. polypropylene, polyester or hi-component fibres. The basis weight of the nonwoven materials contained in the laminate should be between at least 20 and 100 g/m$^2$ and more preferably between 30 and 60 g/m$^2$.

The above mentioned tear strength is measured by the EDANA test method TEAR 70.3-96 with the modification that a conditioning time of 4 h, a temperature of 23° C. and a relative humidity of 50% R.H. is used.

In a preferred embodiment, the belt sections comprise a laminate of at least three layers of non-woven bonded together with ultrasonic welding or heat welding and have a bonding area of less than 10% of the calculated area of the laminate. A bonding area of more than 10% will result in an increased amount of tearing indications or notches and an increased risk for tearing of the belt members. Preferably, the bonding area should be not more than 8%, and more preferably not more than 5%.

The bonding pattern may comprise a plurality of bonding sites in the form of points, lines, spots or the like arranged in a pattern. The bonding area of a bonding pattern is defined as the amount of the pattern that consists of the bonding sites.

Another factor for providing high tear strength is the bonding density, which is the number of bonding sites per unit area. It is preferred that the bonding pattern has a bonding density of between 1 and 15 bonding sites per cm$^2$. Preferably it has a bonding density of between 1 and 10 bonding sites per cm$^2$. With a high bonding density, more tearing indications or notches are formed, which will deteriorate the tearing strength. Relatively large bonding sites, for example in the form of lines, provide a relatively large bonding area with a smaller number of bonding sites, as compared to a bonding pattern of small bonding sites, for example in the form of points, arranged with a higher bonding density. Thus both bonding area and bonding density are important.

One non-limiting example of such a laminate according to this embodiment is a three layered laminate: Carded thermo bonded material, basis weight 30 gsm, PP fibres of 2.2 dtex; Spunbond layer, basis weight 40 gsm, PP fibres of 2.2 dtex; Carded thermo bonded material, basis weight 22 gsm, PP fibres of 2.2 dtex. The spunbond layer is used as the middle layer, the carded material having the highest basis weight is creped and intended to be used as the outside of the belt sections and is adapted to act as loop material (landing zone) for a hook and loop connector, and the carded material having the lowest basis weight is used as inner skin-facing side of the belt sections. The middle spunbond layer is also creped, but with a less distinct creped structure as compared to the carded material intended to be used as the outside of the belt sections. The laminate is bonded by ultrasonic bonding with a bonding area of about 3% and a bonding density of about 7 bonding sites per cm$^2$. The tear strength is 55 N.

The belt sections 30, 32 can have, in a further embodiment, a stiffness value between 10 to 130 g as measured by the ASTMD 40, 32-82 circular bend procedure. The stiffness or flexure resistance of a material sample, in particular of the belt section, is measured by its peak bending stiffness.

The circular bend procedure is a simultaneous multi-directional deformation of a material in which one face of a specimen becomes concave and the other face becomes convex. The circular bend procedure, which is a modified circular bend stiffness test, has the following parts: A smooth-polished steel plate platform which is 102.0×102.0×6.25 mm having an 8.75 mm diameter orifice. The lap edge of the orifice should be at a 45 degree angle to a depth of 3.75 mm. A plunger having an overall length of 72.2 mm, a diameter of 6.25 mm, a ball nose having a radius of 2.97 mm and a needle point extending 0.88 mm there from having a 0.33 mm base diameter and a point having a radius of less than 0.5 mm, the plunger being mounted concentrically with the orifice and having equal clearance on all sides. It should be noted that the needle point is merely to prevent lateral movement of the test specimen, during testing. Therefore, if the needle-point significantly adversely affects the test specimen (for example by puncturing an inflatable structure), the needle-point should not be used. The bottom of the plunger should be set well above the top of the orifice plate. From this position, the downward stroke of the ball nose is to the exact bottom of the plate orifice. A force-measurement gauge and, more specifically, an Instron inverted compression load cell can be used, the load cell having a load range from 0.0 to 2000.0 g. An actuator, in particular Instron Model No. 1122 that has an inverted compression load cell can be used, wherein the Instron 1122 is made by the Instron Engineering Corporation, Canton, Mass.

As has been described above, the belt sections 30, 32 are attached to the absorbent structure 1 in belt attachment portions 34, 36. The belt attachment portions 34, 36 can either be situated on the outside of the absorbent structure 1, namely on the outside of the back-sheet 20 or the outside of the top-sheet 22, or the belt attachment portions can be situated between the top-sheet 22 and the back-sheet 20.

In a preferred embodiment, as it is shown in FIG. 8, the belt attachment portions 34, 36 are designed such that, when each of the belt sections 30, 32 is objected to a tension force of 35 N acting along the longitudinal direction 300 of the belt sections 30, 32 and said longitudinal direction 300 of the belt sections 30, 32 creates an angle α to the lateral direction 110 of the absorbent structure 1, the following minimum average release time (t) of each belt section 30, 32 from the absorbent structure 1 are attained:
when α=10°, t<<720 s;
when α=20°, t<<330 s;
when α=25°, t<<240 s;
when α=30°, t<<180 s; and
when α=40°, t<<75 s.

Accordingly, the belt attachment portions 34, 36 are designed to meet certain minimum requirements. It had been discovered that, for the absorbent article to function satisfactorily, the belt attachment portions 34, 36 should be capable of withstanding a certain tension force applied to the belt sections 30, 32 at the angle α to the lateral direction 110 of the absorbent structure 1 for a certain minimum period of time.

Figure 9:
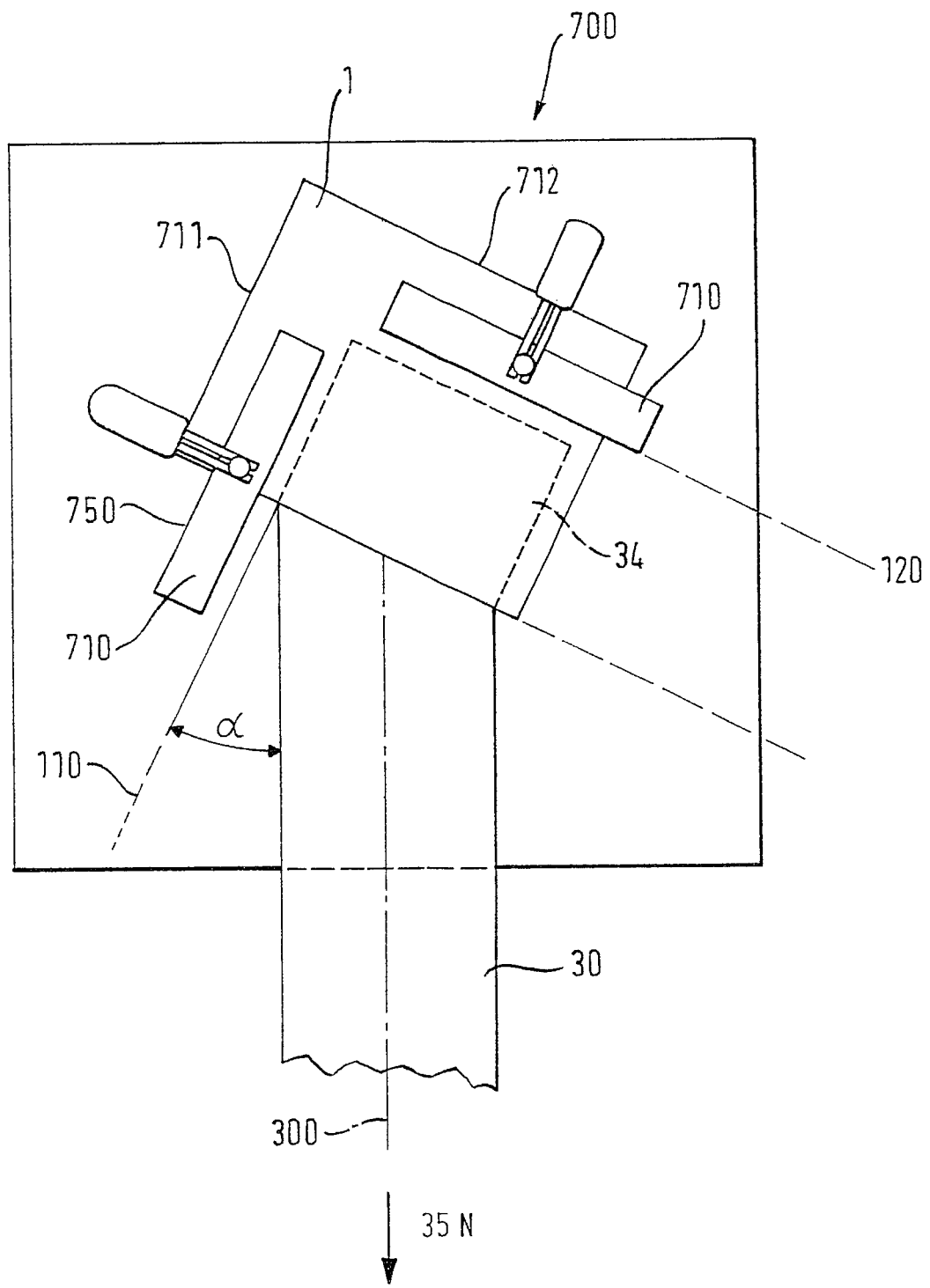
FIG. 9 is a schematic view of a cut out section of the absorbent article being subjected to a test procedure.

Thus, and in a manner which will be explained in greater detail below, the belt attachment portion 34 is subjected to a test procedure such that a portion of the absorbent structure 1 is secured to a test rig 700 shown in FIG. 9 and a load of 35 N is applied to the belt section 30 while the belt section 30 external of the absorbent structure 1 is maintained at a predetermined angle α to the lateral direction 110 of the absorbent structure 1. The absorbent structure 1 is held in the test rig 700 by means of a pair of clamps 710. The time up to failure of the belt attachment portion 34, i.e. when the belt section 30 completely dissociates from the absorbent structure 1, is measured. The time to failure is hereinafter referred to as the release time of the belt attachment portion 34. The minimum average release times are established in the following manner.

A section of the absorbent structure 1, including the back-sheet 20 and the top-sheet 22 and including the belt attachment portion 34 is cut out from the absorbent structure 1. A first cut line 712 is made parallel to the longitudinal direction 120 of the absorbent article 1 at least 45 mm from the end edge of the belt section 30. The first cut line 712 intersects a second cut line 711 extending parallel to the lateral direction 110 of the absorbent article 1 at least 45 mm from the lower edge of the belt section 30. The edges opposite the first cut line 712 and the second cut line 711 correspond to the original outer edges of the absorbent structure 1. The thus cut out section of the absorbent structure including the belt attachment portion 34 is then clamped in the test rig 700 which will be described in greater detail in the following.

The test rig 700 comprises a rectangular base plate to which a rotatable plate 750 is mounted. A pair of clamps 710 spaced at 90° to each other are mounted on the rotatable plate 750. The rotatable 750 plate can be rotated with respect to the rectangular base plate such that suitable values of the angle α are obtainable. The test rig 700 is provided with locking means to enable the rotatable plate 750 to be locked at angular positions at which desired values of α are obtained. The rectangular base plate may be provided with holes to enable the base plate to be maintained in a vertical position on a frame or the like.

Sections are cut out as has been described above from fifty identical absorbent articles. In order to avoid the influence of aging of the articles on the test results, the articles should be no more than 6 months old, i.e. the test is to be performed on articles which have been manufactured during the past six months. The cut out section of a first absorbent structure 1 is secured by the clamps 710 to the test rig 700. The orientation of the cut out section must be such that the clamps clamp the cut out section along lines parallel to the lateral direction 110 and the longitudinal direction 120 of the absorbent structure 1. The edges of the belt section 30 within the absorbent structure 1 are also parallel to the lateral and longitudinal directions, respectively. Thus, these edges are parallel to, and spaced from the clamps 710. The rectangular base plate is held vertically and the rotatable plate 750 is rotated until an angle α of 10° is attained. The rotatable plate 750 is locked at this position and a weight (not shown) is clamped to the free end of the belt section 30. The weight is slowly released until it applies a tension to the belt section 30. The weight is then allowed to hang freely, and a stop watch is started. As soon as the belt section completely dissociates from the absorbent structure 1, i.e., when the weight hits the floor, the stop watch is stopped and the elapsed time is noted. The above procedure is repeated for ten cut out sections at α=10°, α=20°, α=25°, α=30° and α=40°.

The invention claimed is:
1. Absorbent article, the absorbent article comprising:
a longitudinal direction;
an absorbent structure including a back-sheet, a top-sheet, and an absorbent core there between, the absorbent structure having in the longitudinal direction a front portion defining a front lateral edge, a rear portion defining a rear lateral edge and a crotch portion situated between the front portion and the rear portion,
a pair of belt sections for fastening the absorbent article to the waist of a wearer, each of the belt sections being fixedly attached to the rear portion of the absorbent structure at a joint on the rear portion, and at a respective joint, a width of each belt section in the longitudinal direction is less than a width of the rear portion in the longitudinal direction,
wherein the absorbent article has a maximum lateral extension B between the respective lateral-most edges of the belt sections that is governed by the following expression:

$$0.3 < A/B < 0.7$$

where A is the maximum lateral extension of the front lateral edge of the absorbent structure, and
wherein the absorbent structure has a maximum lateral extension C of the rear lateral edge, extending laterally to include the joint, that is governed by the following expression:

$0.8 < C/A < 1.2$.

2. Absorbent article according to claim 1, wherein the dimensions of the absorbent article are governed by the expression $0.35 < A/B < 0.65$.

3. Absorbent article according to claim 2, wherein the dimensions of the absorbent article are governed by the expression $A/B = 0.5$.

4. Absorbent article according to claim 1, wherein the front portion of the absorbent structure includes a first elastic section such that the front portion is generally elastically extendable in the lateral direction of the absorbent structure.

5. Absorbent article according to claim 1, wherein the rear portion includes a second elastic section such that the rear portion is generally elastically extendable in the lateral direction of the absorbent structure.

6. Absorbent article according to claim 1, wherein the absorbent structure includes leg elastics in the crotch portion, such that the crotch portion is generally elastically extendable in the longitudinal direction of the absorbent structure.

7. Absorbent article according to claim 1, wherein the absorbent structure includes elastic front side panels and/or elastic rear side panels such that the side panels are generally extendable at least in the lateral direction of the absorbent structure.

8. Absorbent article according to claim 7, wherein the belt sections are attached to the rear portion of the absorbent structure in belt attachment portions, and the belt attachment portions are generally situated on the elastic rear side panels.

9. Absorbent article according to claim 1, wherein the belt sections are made from a generally non-elastic material.

10. Absorbent article according to claim 1, wherein the absorbent article has a centre-line extending in the longitudinal direction of the absorbent structure and the belt sections are arranged symmetrically with respect to the centre-line.

11. Absorbent article according to claim 10, wherein the absorbent article is generally symmetrical with respect to the centre-line.

12. Absorbent article according to claim 1, wherein both of the belt sections have the same length.

13. Absorbent article according to claim 1, wherein at least one belt connector is situated on each of the belt sections, the belt connector being arranged to be connectable to a landing zone that is situated at the front portion of the absorbent structure.

14. Absorbent article according to claim 13, wherein the belt connectors and the landing zone are made from hook and loop connectors.

15. Absorbent article according to claim 13, wherein the belt connectors are hook connectors and the outer side of a back-sheet comprises an outer layer of nonwoven material, serving as a landing zone.

16. Absorbent article according to claim 13, wherein the belt connectors are hook connectors and the outer side of the belt sections serve as the landing zone.

17. Absorbent article according to claim 1, wherein the belt connectors are adhesive pads and the landing zone is a plastic film.

18. Absorbent article according to claim 1, wherein the absorbent structure has a maximum lateral extension C of the rear lateral edge and the maximum lateral extension A of the front lateral edge and the maximum lateral extension C of the rear lateral edge generally have the same dimensions.

19. Absorbent article according to claim 1, wherein the dimensions of the absorbent structure are governed by the expression $0.85 < C/A < 1.15$.

20. Absorbent article according to claim 19, wherein the dimensions of the absorbent structure are governed by the expression $C/A = 1.0$.

21. Absorbent article according to claim 1, wherein the belt sections are made integral with the back-sheet and/or the top-sheet.

22. Absorbent article according to claim 1, wherein the belt sections are fixedly attached to the outside of the back-sheet and/or the outside of the top-sheet.

23. Absorbent article according to claim 1, wherein the pair of belt sections are made in one piece with one another.

24. Absorbent article according to claim 1, wherein the back-sheet is made from a liquid impermeable but generally vapour permeable material and a nonwoven material.

25. Absorbent article according to claim 24, wherein the liquid impermeable but generally vapour permeable material comprises a laminate of a liquid impermeable but vapour permeable plastic film.

26. Absorbent article according to claim 1, wherein the belt sections comprise a non-woven that has a Shinyakasa-value according to Kawabata of 5 or more.

27. Absorbent article according to claim 1, wherein the belt sections are made of a laminate of at least three layers of non-woven bonded together by ultrasonic welding or heat welding and that have a binding area of less than 10% of the calculated total area of the laminate.

28. Absorbent article according to claim 27, wherein a first layer and a second layer of the laminate have a bulky structure.

29. Absorbent article according to claim 28, wherein the bulky structure is a carded non-woven.

30. Absorbent article according to claim 1, wherein the belt sections have a stiffness value between 10 to 130 g when measured according to the ASTM D 4032-82 circular bend procedure.

31. Absorbent article according to claim 1, wherein the belt sections comprise at least a laminate of two layers of non-woven bonded together by ultrasonic welding or heat welding, whereas the bonding area is less than 10% based on the total area, and the laminate is bonded such as to have a tear strength of at least 22N.

32. Absorbent article according to claim 1, wherein the belt sections are fixedly attached to an outside surface of the back-sheet and/or an outside surface of the top-sheet at the rear portion of the absorbent structure.

33. Absorbent article according to claim 1, wherein each belt section is configured to extend over one hip of the wearer when the absorbent article is properly fitted around the wearer so that the front portion and the rear portion do not overlap on the hips of the wearer, resulting in a gap at each hip of the wearer between the front portion and the rear portion of the absorbent structure when the absorbent article is properly fitted around the wearer.

34. A method of attaching an absorbent article to a wearer having a circumferential waist size X, the absorbent article comprising in a longitudinal direction, a front portion defining a front lateral edge, a rear portion defining a rear lateral edge of length C, and a pair of belt sections each fixedly attached at a joint to the rear portion of the absorbent article for fastening the absorbent article around the waist of a wearer, at a respective joint, a width of each belt section in the longitudinal direction is less than a width of the rear portion in the longitudinal direction, the absorbent article having a maximum lateral extension B between the respective lateralmost edges of the belt sections that is governed by the following expression:

$$0.3 < A/B < 0.7$$

where A is the maximum lateral extension of the front lateral edge of the absorbent structure, and the method comprises:

wrapping the belt section around the waist of the wearer having circumferential waist size satisfying the expression:

$$X > A + C$$

so that the front portion and the rear portion do not overlap on the hip of the wearer, resulting in a gap between the front portion and the rear portion over the hip of the wearer; and fastening an end of the belt sections to the front portion of the absorbent article while maintaining the gap between the front portion and the rear portion of the absorbent over the hip of the wearer.

* * * * *